(12) United States Patent
Dittmar et al.

(10) Patent No.: US 8,703,187 B2
(45) Date of Patent: Apr. 22, 2014

(54) VITAMIN D CONTENT UNIFORMITY IN PHARMACEUTICAL DOSAGE FORMS

(75) Inventors: Gregory Paul Dittmar, Norwich, NY (US); Andrew Irvine Sokolik, Plano, TX (US)

(73) Assignee: Warner Chilcott Company, LLC, Fajardo, PR (US)

( * ) Notice: Subject to any disclaimer, the term of this patent is extended or adjusted under 35 U.S.C. 154(b) by 1601 days.

(21) Appl. No.: 12/148,987

(22) Filed: Apr. 24, 2008

(65) Prior Publication Data

US 2009/0022792 A1  Jan. 22, 2009

Related U.S. Application Data

(60) Provisional application No. 60/926,133, filed on Apr. 25, 2007.

(51) Int. Cl.
*A61K 9/20* (2006.01)

(52) U.S. Cl.
USPC .......................................... 424/464; 514/167

(58) Field of Classification Search
None
See application file for complete search history.

(56) References Cited

U.S. PATENT DOCUMENTS

| 4,729,895 | A | | 3/1988 | Makino et al. |
| 5,290,561 | A | * | 3/1994 | Farhadieh et al. ............ 424/449 |
| 5,328,903 | A | | 7/1994 | Ishii et al. |
| 6,254,904 | B1 | | 7/2001 | Bailey et al. |
| 7,067,154 | B1 | | 6/2006 | Valleri et al. |
| 2005/0232989 | A1 | * | 10/2005 | Piene et al. .................... 424/464 |
| 2007/0110800 | A1 | * | 5/2007 | Gierer ........................... 424/451 |

FOREIGN PATENT DOCUMENTS

| EP | 0872240 B1 | 7/2002 |
| JP | 2001-511453 A | 8/2001 |
| JP | 2003-81876 A | 3/2003 |
| JP | 2005-517720 A | 6/2005 |
| JP | 2006-63030 A | 3/2006 |
| JP | 2008-516639 A | 5/2008 |
| WO | WO 92/09271 | 6/1992 |
| WO | 2003/070217 A1 | 8/2003 |
| WO | WO 2005034919 A2 * | 4/2005 |
| WO | 2005/123569 A2 | 12/2005 |

OTHER PUBLICATIONS

"Insights into the Role of Electrostatic Forces on the Behavior of Dry Pharmaceutical Particulate Systems," Lachiver, E., et al., Pharmaceutical Research 23(5): 997 - 1007 (2006).*
"Quantitative Characterization of Mixing of Dry Powders in V-Blenders," Brone, D., et al., Particle Technology and Fluidization 44(2): 271 - 278 (1998).*
"Significance of drug content and of drug proportion to the content uniformity of solid dosage forms," Acta Pharma. Jugosl. 33: 279 - 286 (1988).*
"Evaluation of the content uniformity and dispersion properties of fluticasone DPI compositions," Sebti, T., et al., J. Drug Del. Sci. Tech. 17(3): 223 - 229 (2007).*
"Segregation of Active Constituents from Tablet Formulations During Grinding: Theoretical Considerations," Drug Development and Industrial Pharmacy 8(4): 565 - 578 (1982).*
International Search Report.
Pharmaceutical Engineering, first edition, Chijin Shokan Co., Ltd., pp. 228-235 (1971).
Office Action issued in Japanese Patent Application No. 2010-504961, dated Nov. 6, 2012 (3 pages).
Office Action issued in Japanese Patent Application No. 2010-504961, dated May 29, 2012 (5 pages).

* cited by examiner

*Primary Examiner* — David J Blanchard
*Assistant Examiner* — Daniel F Coughlin
(74) *Attorney, Agent, or Firm* — Fitzpatrick, Cella, Harper & Scinto

(57) ABSTRACT

New dosage forms of vitamin D and calcium carbonate having improved content uniformity are described. The improvements are realized through modifications to the formulation, the raw material specifications, and the process of manufacture.

17 Claims, 7 Drawing Sheets

VITAMIN D CONTENT UNIFORMITY IN PHARMACEUTICAL DOSAGE FORMS

CROSS REFERENCE TO RELATED APPLICATIONS

This application claims the benefit of U.S. Provisional Application No. 60/926,133, filed on Apr. 25, 2007.

TECHNICAL FIELD

The present invention is directed to new dosage forms of Vitamin D having improved content uniformity. The improvements are realized through modifications to the formulation, the raw material specifications, and the process of manufacture.

BACKGROUND OF THE INVENTION

Content uniformity is a regulatory concern for all finished pharmaceutical products. This is particularly true for solid oral dosage forms such as tablets and capsules. While typical regulatory requirements may not be as rigorous for nutritional supplements such as vitamins, where vitamins are packaged with another pharmaceutical product, content uniformity requirements become rigorous for all components.

Anytime that a vitamin is added to any pharmaceutical formulation it will be present in very low quantities by weight (typically from 0.001 to 0.05 percent). Therefore meeting the pharmaceutical requirements for content uniformity of <6% relative standard deviation (RSD) is a major challenge. Most of the combination vitamin products on the market today only have to meet nutritional standards that have no content uniformity requirement. Typical calcium plus vitamin D nutritional products currently on the market have content uniformity for vitamin D of 7-15% RSD. The FDA has been clear that any pharmaceutical product or nutritional product packaged with another pharmaceutical product must meet all pharmaceutical specifications. Formulations of calcium carbonate and vitamin D have been problematic in terms of acceptable content uniformity.

Dosage forms comprising vitamin D have been discussed in the prior art. Much of the prior art has been concerned with the stability of vitamin D dosage forms. Makino et al, in U.S. Pat. No. 4,729,895 teaches solid pharmaceutical preparations of vitamins $D_3$ prepared by forming an outer layer comprising vitamin $D_3$ and an excipient, which is readily soluble in an organic solvent, around an inner layer comprising an excipient which is slightly soluble in an organic solvent. Makino teaches markedly improved stability for such solid pharmaceutical preparations of vitamins $D_3$.

In U.S. Pat. No. 5,328,903, Ishii, et al. teaches a composition for solid pharmaceutical dosage forms of vitamin D in which the vitamin D is uniformly distributed in the composition. The composition comprises an excipient comprising mannitol and/or sugar; a degradative agent comprising hydroxypropyl cellulose; and/or a binder comprising polyvinyl pyrrolidone and/or hydroxypropylmethyl cellulose.

In PCT publication WO 92/09271, Wozny, et al. teaches solid pharmaceutical preparations containing vitamin $D_3$ which are significantly stabilized. The compositions include hydroxypropylmethyl cellulose to which is attached active vitamin $D_3$ and a polymer which is readily soluble in an organic solvent.

The inventors have found that by modifying the formulation, raw material specifications, and the process, we can improve the content uniformity and meet pharmaceutical specifications.

BRIEF SUMMARY OF THE INVENTION

The present invention is directed to improved formulations of vitamin D that meet pharmaceutical specifications with respect to content uniformity as measured by standard compendial (i.e., United States Pharmacopeia (USP)) content uniformity tests. A secondary benefit is that more stringent content uniformity will reduce variation in stability tests which can result in increased shelf life and/or reduced overages.

In one aspect of the present invention, there is a method of manufacturing vitamin D containing tablets comprising forming a premix comprising a mixture of vitamin D granulation and silicon dioxide; adding a second nutritional or pharmaceutical active component ("second component") that has a size ratio to the vitamin D component of at least about 1.4, preferably at least about 1.5, to said premix to form a first vitamin D/second component granulation mixture; mixing and sieving the first vitamin D/second component granulation mixture; blending the first vitamin D/second component granulation mixture in a V blender; dividing the first vitamin D/second component granulation mixture into four equal portions and adding the second component to each portion to form a second vitamin D/second component granulation mixture; blending the second vitamin D/second component granulation mixture in a V blender; and, forming tablets from a composition comprising the second vitamin D/second component granulation mixture. In some embodiments, the premix of vitamin D and silicon dioxide is in a mass ratio of about 25:9 vitamin D:silicon dioxide. In some embodiments, the first mixture is in a mass ratio of about 1000:25:9 second component:vitamin D:silicon dioxide. In some embodiments, the step of mixing and sieving comprises sieving through a US 20 Mesh sieve. In some embodiments, the step of blending the first mixture in a 16 quart V blender comprises blending for about 2 minutes. The step of dividing the first mixture into four equal portions and adding the second component may comprise adding 2.0 kg of the second component. In some embodiments, the method further comprises the step of milling and sieving the second component granulation to produce second component and vitamin D granulations having median particle sizes within ±40% of one another. The median particle sizes are more preferably within ±25% of one another. The median particle sizes are most preferably within ±15% of one another. In preferred embodiments, the method further comprises the step of milling and sieving the second component granulation to have a $D_{20}$ value of less than 110 microns. In preferred embodiments, the method further comprises the step of milling and sieving the second component granulation to have a $D_{16}$ value of less than 95 microns.

In another aspect of the present invention, there is a method of manufacturing calcium carbonate/vitamin D tablets comprising forming a premix comprising a mixture of vitamin D granulation and silicon dioxide; adding a calcium carbonate granulation to said premix to form a first vitamin D/calcium carbonate granulation mixture; mixing and sieving the first vitamin D/calcium carbonate granulation mixture; blending the first vitamin D/calcium carbonate granulation mixture in a V blender; dividing the first vitamin D/calcium carbonate granulation mixture into four equal portions and adding calcium carbonate to each portion to form a second vitamin D/calcium carbonate granulation mixture; blending the second vitamin D/calcium carbonate granulation mixture in a V blender; and, forming tablets from a composition comprising the second vitamin D/calcium carbonate granulation mixture. In some embodiments, the premix of vitamin D and silicon dioxide is in a mass ratio of about 25:9 vitamin D:silicon dioxide. In some embodiments, the first mixture is in a mass ratio of about 1000:25:9 calcium carbonate:vitamin D:silicon dioxide. In some embodiments, the step of mixing and sieving comprises sieving through a US 20 Mesh sieve. In some embodiments, the step of blending the first mixture in a 16 quart V blender comprises blending for about 2 minutes. The step of dividing the first mixture into four equal portions and adding calcium carbonate may comprise adding 2.0 kg of calcium carbonate. In some embodiments, the method further comprises the step of milling and sieving the calcium carbonate granulation to produce calcium carbonate and vitamin D granulations having median particle sizes within ±40% of one another. The median particle sizes are more preferably within ±25% of one another. The median particle sizes are most preferably within ±15% of one another. In preferred embodiments, the method further comprises the step of milling and sieving the calcium carbonate granulation to have a $D_{20}$ value of less than 110 microns. In preferred embodiments, the method further comprises the step of milling and sieving the calcium carbonate granulation to have a $D_{16}$ value of less than 95 microns.

In another aspect of the present invention, there is a method of manufacturing calcium carbonate/vitamin D tablets comprising forming a premix comprising a layer of calcium carbonate, a layer of vitamin D/silicon dioxide and another layer of calcium carbonate; sieving and blending the premix to form a first vitamin D/calcium carbonate granulation mixture; adding calcium carbonate to the first vitamin D/calcium carbonate granulation mixture such that there is a layer of calcium carbonate granulation, a layer of the first granulation mixture, and another layer of calcium carbonate to form a second vitamin D/calcium carbonate granulation mixture; sieving and blending the second vitamin D/calcium carbonate granulation mixture; and forming tablets from a composition comprising the second vitamin D/calcium carbonate granulation mixture. In preferred embodiments, one or both of the steps of sieving and blending the premix and sieving and blending the second vitamin D/calcium carbonate granulation mixture comprises blending with a Comil. In some embodiments, one or both of the steps of sieving and blending the premix and sieving and blending the second vitamin D/calcium carbonate granulation mixture comprises blending with a V blender. In some embodiments, the step of sieving and blending the premix comprises blending with a V blender comprises blending for about 8 minutes. In some embodiments, the step of sieving and blending the second vitamin D/calcium carbonate granulation mixture comprises blending with a V blender comprises blending for about 50 minutes. In some embodiments, the step of forming a premix comprising a layer of calcium carbonate, a layer of vitamin D/silicon dioxide, and another layer of calcium carbonate comprises adding two layers of about 500 kg each of calcium carbonate. In some embodiments, the first mixture is in a mass ratio of about 1600:20:7 calcium carbonate:vitamin D:silicon dioxide.

In another aspect of the present invention, there is a pharmaceutical tablet of calcium carbonate and vitamin D produced by the process comprising forming a premix comprising a mixture of vitamin D granulation and silicon dioxide; adding a calcium carbonate granulation to said premix to form a first vitamin D/calcium carbonate granulation mixture; mixing and sieving the first vitamin D/calcium carbonate granulation mixture; blending the first vitamin D/calcium carbonate granulation mixture in a V blender; dividing the first vitamin D/calcium carbonate granulation mixture into four equal portions and adding calcium carbonate each portion to form a second vitamin D/calcium carbonate granulation mixture; blending the second vitamin D/calcium carbonate granulation mixture in a V blender; and, pressing a composition comprising the second vitamin D/calcium carbonate granulation mixture into a tablet. In some embodiments, the premix of vitamin D and silicon dioxide is in a mass ratio of about 25:9 vitamin D:silicon dioxide. In some embodiments, the first mixture is in a mass ratio of about 1000:25:9 calcium carbonate:vitamin D:silicon dioxide. In some embodiments, the step of mixing and sieving comprises sieving through a US 20 Mesh sieve. In some embodiments, the step of blending the first mixture in a V blender comprises blending for about 2 minutes. In some embodiments, the step of dividing the first mixture into four equal portions and adding calcium carbonate comprises adding 2.0 kg of calcium carbonate. In some embodiments, the method further comprises the step of milling and sieving the calcium carbonate granulation to produce calcium carbonate and vitamin D granulations having median particle sizes within ±40% of one another. More preferably, the median particle sizes are within ±25% of one another. Most preferably, the median particle sizes are within ±15% of one another. In preferred embodiments, the process further comprises the step of milling and sieving the calcium carbonate granulation to have a $D_{20}$ value of less than 110 microns. In preferred embodiments, the process further comprises the step of milling and sieving said calcium carbonate granulation to have a $D_{16}$ value of less than 95 microns.

In another aspect of the present invention, there is a pharmaceutical tablet of calcium carbonate and vitamin D produced by the process comprising forming a premix comprising a layer of calcium carbonate, a layer of vitamin D/silicon dioxide and another layer of calcium carbonate; sieving and blending the premix to form a first vitamin D/calcium carbonate granulation mixture; adding calcium carbonate to the first vitamin D/calcium carbonate granulation mixture such that there is a layer of calcium carbonate granulation, a layer of the first granulation mixture, and another layer of calcium carbonate, to form a second vitamin D/calcium carbonate granulation mixture; sieving and blending the second vitamin D/calcium carbonate granulation mixture; and forming tablets from a composition comprising the second vitamin D/calcium carbonate granulation mixture. In preferred embodiments, one or both of the steps of sieving and blending the premix and sieving and blending the second vitamin D/calcium carbonate granulation mixture comprises blending with a Comil. In some embodiments, one or both of said steps of sieving and blending the premix and sieving and blending the second vitamin D/calcium carbonate granulation mixture comprises blending with a V blender. In some embodiments, the step of sieving and blending the premix comprises blending with a V blender comprises blending for about 8 minutes. In some embodiments, the step of sieving and blending the second vitamin D/calcium carbonate granulation mixture comprises blending with a V blender comprises blending for about 50 minutes. In some embodiments, the step of forming a premix comprising a layer of calcium carbonate, a layer of vitamin D/silicon dioxide and another layer of calcium carbonate comprises adding two layers of about 500 kg each of calcium carbonate. In some embodiments, the first mixture is in a mass ratio of about 1600:20:7 calcium carbonate:vitamin D:silicon dioxide.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

As used herein, "a" or "an" means one or more. Unless otherwise indicated, the singular contains the plural and the plural contains the singular.

The theoretical best content uniformity can be calculated based on the number of particles per scale of scrutiny (in this case a tablet). In general a robust pharmaceutical tablet has >10,000 particles per unit of scrutiny and results in an actual content uniformity RSD of 1-2%. The standard vitamin tablet formulation has 150-200 vitamin granules per unit of scrutiny and results in a theoretical best RSD of 5-7%. In reality content uniformity of vitamin tablets have an RSD of 7-15%. Any thing that increases the number of particles of vitamin per gram will improve content uniformity RSD (e.g. screening out the larger vitamin particles from the vitamin premix, reducing the vitamin premix potency, increasing the vitamin assay per tablet (e.g. 400 IU to 800 IU)).

If one wet or dry granulates the vitamin with a carrier like lactose, maltodextrin, etc and then mills the granulation, one can increase the number of vitamin particle which then improves the theoretical content uniformity RSD. It has also been found that if the vitamin premix is milled so that there are more particles per gram of premix, the content uniformity RSD can be reduced. Additionally, a lower strength (IU/gram) vitamin premix results in an increase in the number of particle per gram and a lower content uniformity RSD.

The theoretical calculation assumes that the mixing process is perfect and that there is no segregation after the powders are mixed. We have found that vitamin premixes have a static charge that inhibits mixing. By adding silicon dioxide, we reduce the static charge and promote thorough mixing. Additionally by matching the particle size distribution (PSD) of the second component and the vitamin premix powder, we can minimize the segregation potential of a powder blend.

Figure 1:
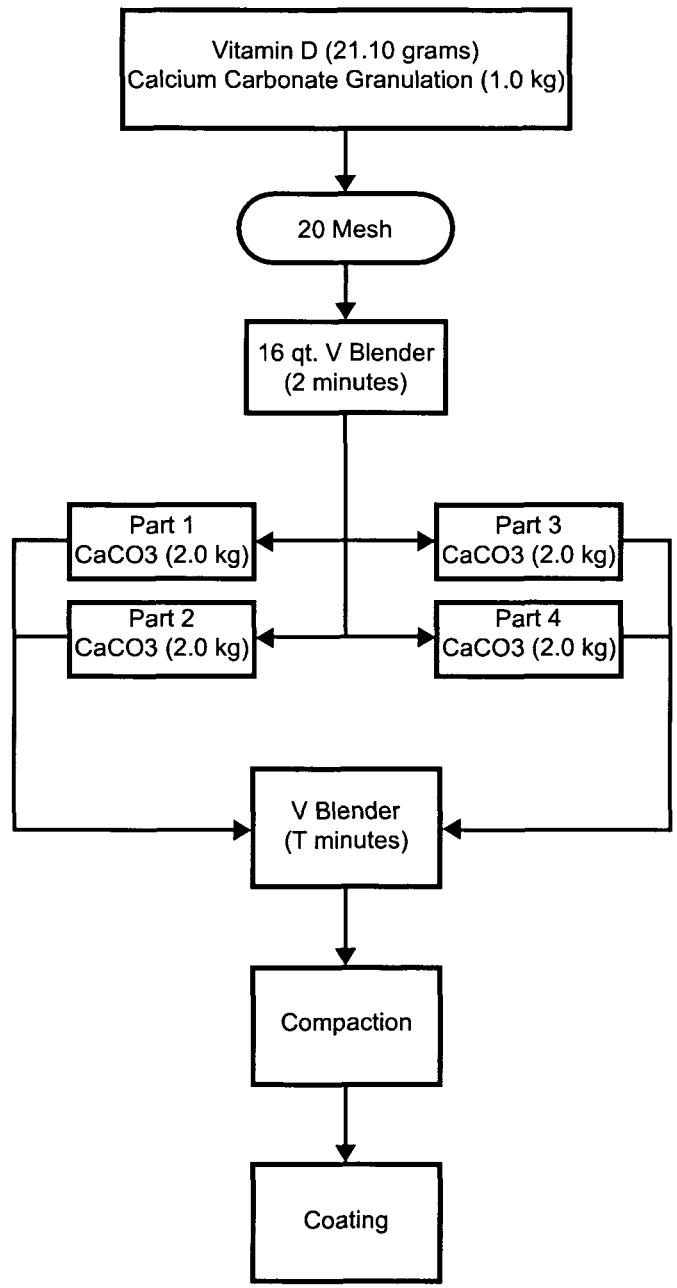
FIG. 1 is a block flow diagram of the standard process (trial 1) for calcium carbonate/vitamin D tablets.

The vitamin D3 may be any vitamin D3 source but as used in the examples herein is supplied by BASF as beadlets with a potency of 100 IU/mg or 50 IU/mg. The standard process (trial 1) for the small scale manufacture of calcium carbonate/vitamin D tablets is illustrated in the flow diagram of FIG. 1. 21.1 g of vitamin D and 1.0 kg of calcium carbonate are mixed and sieved through US 20 Mesh. The resulting mixture is introduced into a 16 qt. V blender and blended for 2 minutes. The blended mixture is then divided into four equal portions and each portion is mixed with 2.0 kg of calcium carbonate. The portions are combined and introduced into a V blender. The blending times are varied and the result reported herein. Five blend times a reevaluated for tablet uniformity: 15, 20, 25, and 30 minutes. Tablets are manufactured by compaction and coating of the resulting blend.

The second component of the pharmaceutical dosage forms herein may be a nutritional component and/or a pharmaceutical active component with a particle size ratio of at least 1.4, preferably at least 1.5, the particle size of the vitamin D3. Such components include but are not limited to calcium carbonate, calcium phosphate, or calcium citrate maleate.

Figure 2:
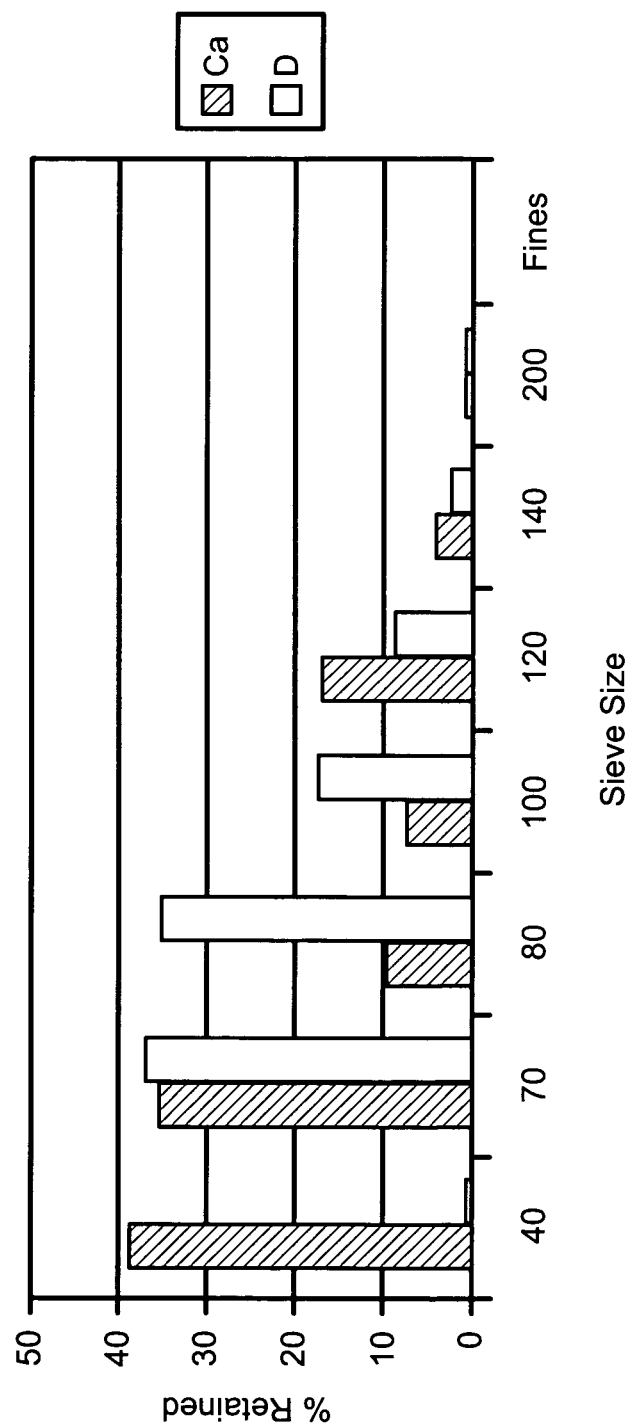
FIG. 2 illustrates the particle size profile for calcium carbonate and vitamin D for the standard process.

Particle size analyses are performed for the second component granulation, including but not limited to calcium carbonate, calcium phosphate and calcium citrate maleate, and for vitamin D. One hundred gram samples are tested in a ro-tap apparatus. Material is sieved through 40, 70, 80, 100, 120, 140, and 200 US Mesh Sieves. The data is provided below in tabular form and graphically in FIG. 2. A measurement of particle size distribution is the mean particle size of a powder sample. Another preferred measurement of particle size distribution is the median particle size, denoted $D_{50}$. Another preferred measurement of particle size distribution is the size for the smallest 16% ($D_{16}$) and 20% ($D_{20}$) of the particle size distribution.

TABLE 1

Calcium Carbonate Particle Size Analysis Trial 1.
CALCIUM CARBONATE GRANULATION
Sample Size: 100 g

| US Mesh | Microns | Gross Wt. (g) | Tare Wt. (g) | Net Wt (g) | Percent Retained |
|---|---|---|---|---|---|
| 40 | 425 | 394.88 | 355.96 | 38.92 | 38.904 |
| 70 | 212 | 374.06 | 350.47 | 23.59 | 23.581 |
| 80 | 177 | 409.36 | 399.77 | 9.59 | 9.586 |
| 100 | 150 | 362.44 | 354.92 | 7.52 | 7.517 |
| 120 | 125 | 363.14 | 346.63 | 16.51 | 16.503 |
| 140 | 106 | 310.17 | 306.45 | 3.72 | 3.719 |
| 200 | 75 | 337.57 | 337.39 | 0.18 | 0.180 |
| Fines | | 378.77 | 378.76 | 0.01 | 0.010 |
| | | | Total | 100.04 | 100 |

$D_{50}$ 306 micron

TABLE 2

Vitamin D Particle Size Analysis Trial 1.
PARTICLE SIZE ANALYSIS - VITAMIN D
Sample Size: 100 g

| US Mesh | Microns | Gross Wt. (g) | Tare Wt. (g) | Net Wt. (g) | Percent Retained |
|---|---|---|---|---|---|
| 40 | 425 | 356.28 | 355.79 | 0.49 | 0.489 |
| 70 | 212 | 387.09 | 350.28 | 36.81 | 36.733 |
| 80 | 177 | 434.15 | 398.89 | 35.26 | 35.186 |
| 100 | 150 | 370.72 | 353.75 | 16.97 | 16.934 |
| 120 | 125 | 354.19 | 345.53 | 8.66 | 8.642 |
| 140 | 106 | 307.27 | 305.45 | 1.82 | 1.816 |
| 200 | 75 | 337.15 | 336.96 | 0.19 | 0.190 |
| Fines | | 378.74 | 378.73 | 0.01 | 0.010 |
| | | | Total | 100.21 | 100 |

$D_{50}$ 199 micron

The ratio of the calcium carbonate $D_{50}$ (306 microns) and the vitamin D $D_{50}$ (199 microns) is 1.54. Blend uniformity studies are conducted with tablets manufactured at a 20% overage of vitamin D and blend times of 15, 20, 25 and 30 minutes.

TABLE 3

Blend Uniformity for 20% Overage; 15 Minute Blend Time; Target Weight of 1.423 g.

| | % Label Claim | Wt. (g) | % Wt. | Wt. Adjusted Assay |
|---|---|---|---|---|
| | 106 | 1.4422 | 101.3 | 104.6 |
| | 112 | 1.445 | 101.5 | 110.3 |
| | 111 | 1.4373 | 101.0 | 109.9 |
| | 105 | 1.4338 | 100.8 | 104.2 |
| | 112 | 1.4316 | 100.6 | 111.3 |
| | 113 | 1.4342 | 100.8 | 112.1 |
| | 105 | 1.4345 | 100.8 | 104.2 |
| | 104 | 1.4303 | 100.5 | 103.5 |
| | 107 | 1.4371 | 101.0 | 106.0 |
| | 107 | 1.4401 | 101.2 | 105.7 |
| AVERAGE | 108.2 | 1.43661 | | 107.2 |
| STDEV | 3.43 | 0.00 | | 3.35 |
| RSD | 3.17 | 0.33 | | 3.12 |

TABLE 4

Blend Uniformity for 20% Overage; 20 Minute Blend Time; Target Weight of 1.423 g.

| | % Label Claim | Wt. (g) | % Wt. | Wt. Adjusted Assay | *DUPLICATE* |
|---|---|---|---|---|---|
| | 121 | 1.4372 | 101.0 | 119.8 | 108 |
| | 113 | 1.4142 | 99.4 | 113.7 | 133 |
| | 110 | 1.4174 | 99.6 | 110.4 | 111 |
| | 116 | 1.4353 | 100.9 | 115.0 | 124 |
| | 123 | 1.437 | 101.0 | 121.8 | 138 |
| | 136 | 1.4235 | 100.0 | 136.0 | 102 |
| | 112 | 1.4163 | 99.5 | 112.5 | 121 |
| | 127 | 1.4221 | 99.9 | 127.1 | 107 |
| | 134 | 1.4318 | 100.6 | 133.2 | 105 |
| | 129 | 1.4262 | 100.2 | 128.7 | 116 |
| AVERAGE | 122.1 | 1.4261 | | 121.8 | 116.5 |
| STDEV | 9.29 | 0.01 | | 9.04 | 12.23 |
| RSD | 7.61 | 0.62 | | 7.42 | 10.50 |

*Duplicate analysis performed to verify results

TABLE 5

Blend Uniformity for 20% Overage; 25 Minute Blend Time; Target Weight of 1.423 g.

| | % Label Claim | Wt. (g) | % Wt. | Wt. Adjusted Assay |
|---|---|---|---|---|
| | 108 | 1.4377 | 101.0 | 106.9 |
| | 132 | 1.4308 | 100.5 | 131.3 |
| | 116 | 1.4375 | 101.0 | 114.8 |
| | 103 | 1.4368 | 101.0 | 102.0 |
| | 98 | 1.4308 | 100.5 | 97.5 |
| | 106 | 1.4339 | 100.8 | 105.2 |
| | 99 | 1.4311 | 100.6 | 98.4 |
| | 109 | 1.4338 | 100.8 | 108.2 |
| | 94 | 1.4318 | 100.6 | 93.4 |
| | 105 | 1.4367 | 101.0 | 104.0 |
| AVERAGE | 107.0 | 1.43409 | | 106.2 |
| STDEV | 10.78 | 0.00 | | 10.70 |
| RSD | 10.08 | 0.20 | | 10.08 |

TABLE 6

Blend Uniformity for 20% Overage; 30 Minute Blend Time; Target Weight of 1.423 g.

| | % Label Claim | Wt. (g) | % Wt. | Wt. Adjusted Assay |
|---|---|---|---|---|
| | 116 | 1.4331 | 100.7 | 115.2 |
| | 107 | 1.4294 | 100.4 | 106.5 |
| | 118 | 1.4328 | 100.7 | 117.2 |
| | 112 | 1.4378 | 101.0 | 110.8 |
| | 109 | 1.4387 | 101.1 | 107.8 |
| | 121 | 1.4376 | 101.0 | 119.8 |
| | 116 | 1.4303 | 100.5 | 115.4 |
| | 123 | 1.4344 | 100.8 | 122.0 |
| | 107 | 1.4311 | 100.6 | 106.4 |
| | 122 | 1.4364 | 100.9 | 120.9 |
| AVERAGE | 115.1 | 1.43416 | | 114.2 |
| STDEV | 6.08 | 0.00 | | 5.96 |
| RSD | 5.28 | 0.23 | | 5.22 |

Figure 3:
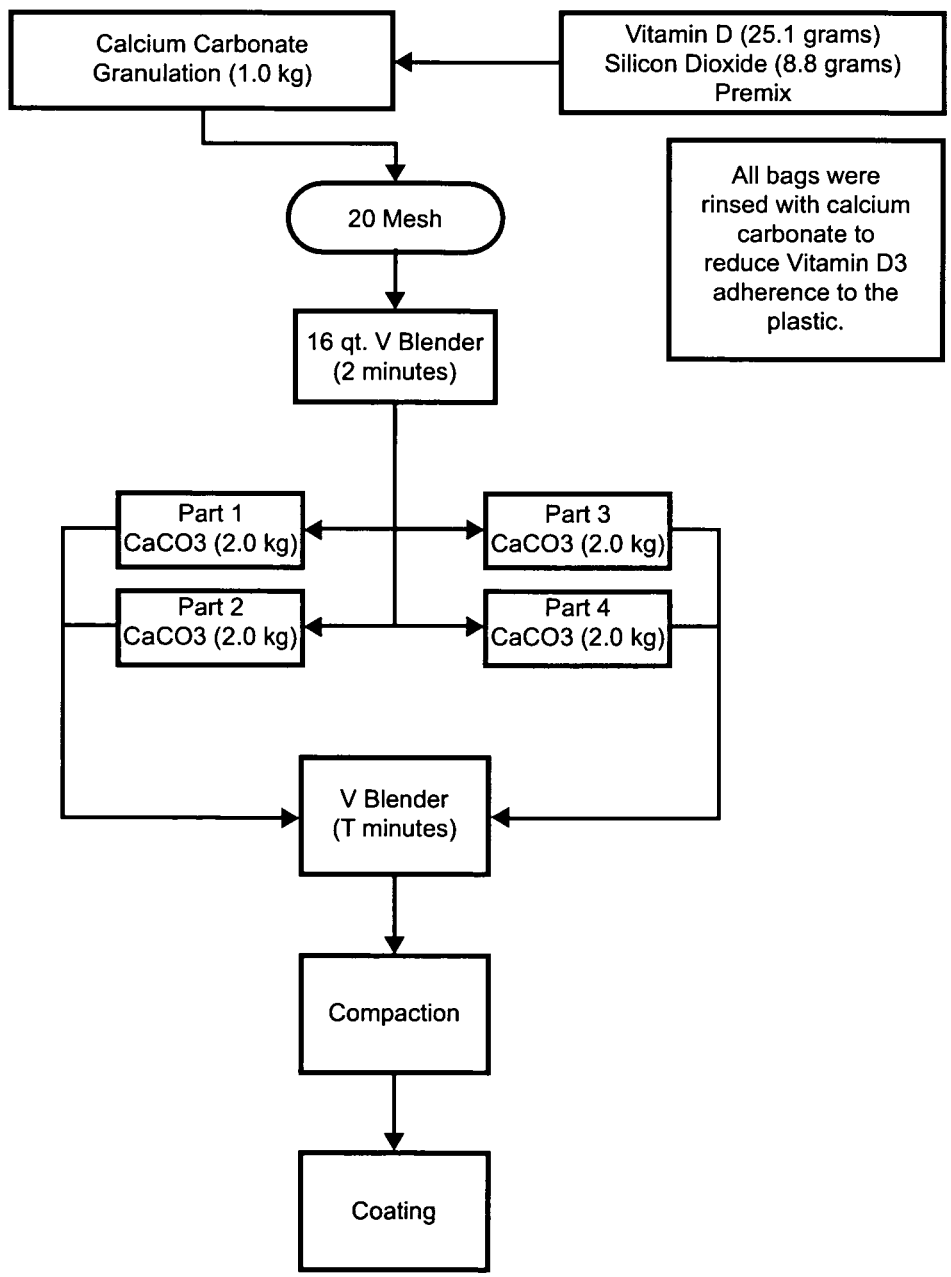
FIG. 3 is a block flow diagram of the modified process.

Following this standard procedure, low recovery of vitamin D may occur and the variability may be high as vitamin D has an affinity for plastic materials such as plastic bags that may be used in the manufacturing. [0033] A modified manufacturing process (trial 2) is used to improve recovery and content uniformity of vitamin D/calcium carbonate tablets. The modified process for the small scale manufacture of calcium carbonate/vitamin D tablets is illustrated in the flow diagram of FIG. 3. In the modified process, a premix of vitamin D (25.1 g) and silicon dioxide (8.8 g) is made and this is added to 1.0 kg of calcium carbonate granulation. The silicon dioxide is added in an attempt to minimize or eliminate the electrostatic interaction of vitamin D with the surfaces in which it comes into contact in the manufacturing process of vitamin D tablets. The mixture is then mixed and sieved through US 20 Mesh. The resulting mixture is introduced into a 16 qt. V blender and blended for 2 minutes. The blended mixture is then divided into four equal portions and each portion is mixed with 2.0 kg of calcium carbonate. The portions are combined and introduced into a V blender. The blending times are varied and the results reported herein. Vitamin D at a 20% overage and the same blend times are evaluated for tablet uniformity: 15, 20, 25, and 30 minutes. Tablets are manufactured by compaction and coating of the resulting blend.

The match between $D_{50}$ values is preferably about ±40%, more preferably about ±25%, and most preferably about ±15% to achieve good content uniformity. If one of the components, for example, the calcium carbonate had a $D_{50}$ of 200 microns then the vitamin D component should have a $D_{50}$ of 120-280 microns, more preferably 150-250 microns, and most preferably 170-230 microns.

Figure 4:
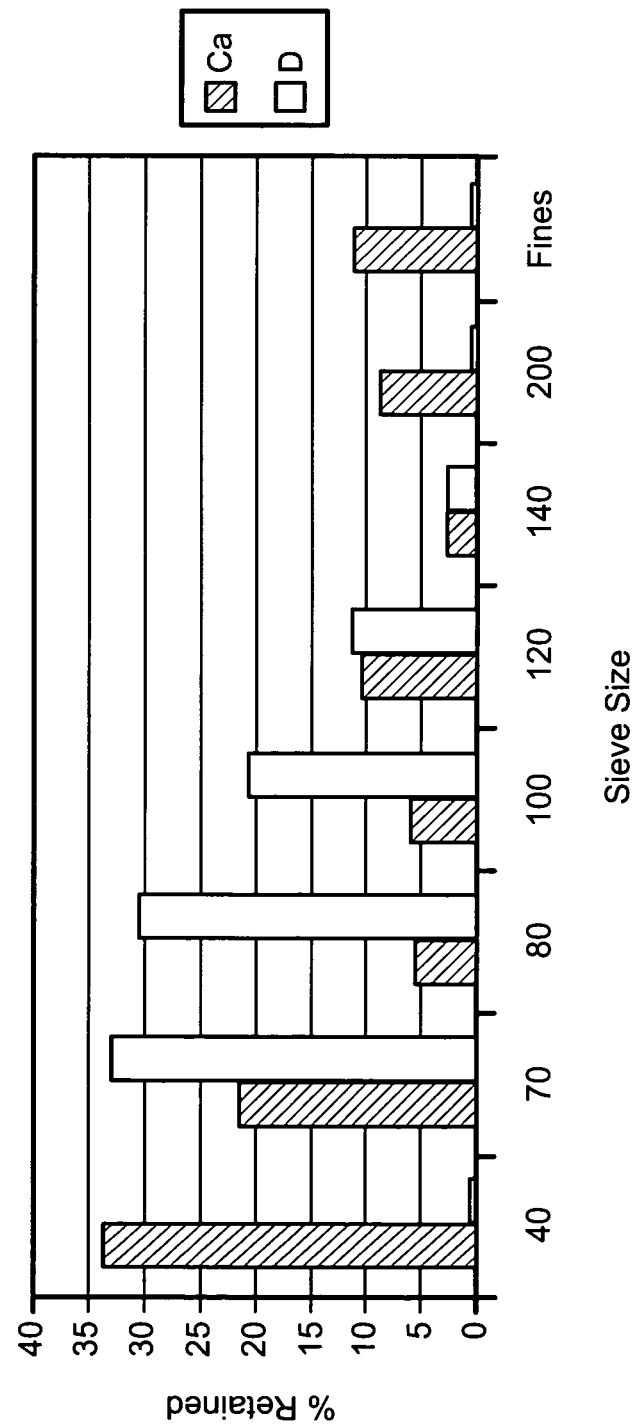
FIG. 4 illustrates the particle size profile for calcium carbonate and vitamin D for the modified process.

The particle size profile of the calcium carbonate is modified to more closely match the vitamin D particle size profile by appropriate milling and sieving. The particle size data is provided below, and is provided in graphical form in FIG. 4 for calcium carbonate and vitamin D.

TABLE 7

Calcium Carbonate Particle Size Analysis Trial 2.
PARTICLE SIZE ANALYSIS - CALCIUM CARBONATE
Sample Size: 100 g

| US Mesh | Microns | Gross | Tare | Net | Percent Retained |
|---|---|---|---|---|---|
| 40 | 425 | 419.3 | 385.5 | 33.8 | 33.868 |
| 70 | 212 | 372 | 350.3 | 21.7 | 21.743 |
| 80 | 177 | 404.7 | 398.9 | 5.8 | 5.812 |
| 100 | 150 | 358.9 | 353.6 | 5.3 | 5.311 |
| 120 | 125 | 356 | 345.4 | 10.6 | 10.621 |
| 140 | 106 | 307.9 | 305.3 | 2.6 | 2.605 |
| 200 | 75 | 345.7 | 336.9 | 8.8 | 8.818 |
| Fines | | 389.9 | 378.7 | 11.2 | 11.222 |
| | | | Total | 99.8 | 100 |

$D_{50}$ 254 micron

TABLE 8

Vitamin D Particle Size Analysis Trial 2.
PARTICLE SIZE ANALYSIS - VITAMIN D
Sample Size: 25.6 g

| US Mesh | Microns | Gross | Tare | Net | Percent Retained |
|---|---|---|---|---|---|
| 40 | 425 | 385.5 | 385.4 | 0.1 | 0.392 |
| 70 | 212 | 358.7 | 350.3 | 8.4 | 32.941 |
| 80 | 177 | 406.9 | 399 | 7.9 | 30.980 |
| 100 | 150 | 359.1 | 353.8 | 5.3 | 20.784 |
| 120 | 125 | 348.5 | 345.6 | 2.9 | 11.373 |
| 140 | 106 | 306 | 305.3 | 0.7 | 2.745 |
| 170 | 90 | 0 | 0 | 0 | 0.000 |
| 200 | 75 | 337.1 | 337 | 0.1 | 0.392 |
| 230 | 63 | 0 | 0 | 0 | 0.000 |
| 270 | 53 | 0 | 0 | 0 | 0.000 |
| 400 | 38 | 0 | 0 | 0 | 0.000 |
| Fines | | 378.7 | 378.6 | 0.1 | 0.392 |
| | | | Total | 25.5 | 100 |

$D_{50}$ 193 micron

In the modified processes, the calcium carbonate granulation is milled and sieved in such a way as to give a particle size distribution that more closely matches the vitamin D particle size distribution. This can be seen when comparing FIG. 2 (trial 1) and FIG. 4 (trial 2). The particle size profiles of calcium carbonate and vitamin D more closely match one another in the modified process. The ratio of the calcium carbonate $D_{50}$ (254 micron) and the vitamin D $D_{50}$ (193 micron) is now 1.32.

Figure 5:
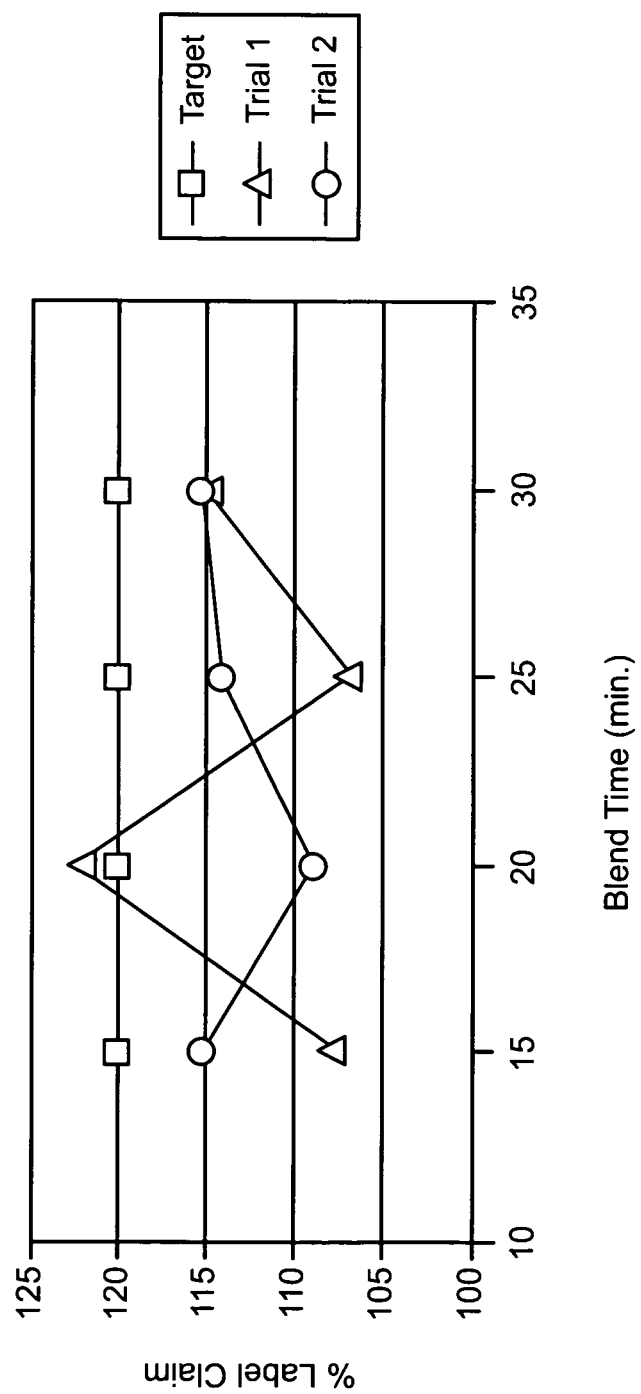
FIG. 5. illustrates recovery (composite assay) for the standard and modified processes as a function of blend time.

The improvement in recovery for the modified process can be seen in FIG. 5, which graphically presents recovery in % of label claims versus blend time for blend times of 15, 20, 25, and 30 minutes for both trial 1 and trial 2. While results continue to be lower than target, they are more consistent and closer to target than that seen in the standard process.

Figure 6:
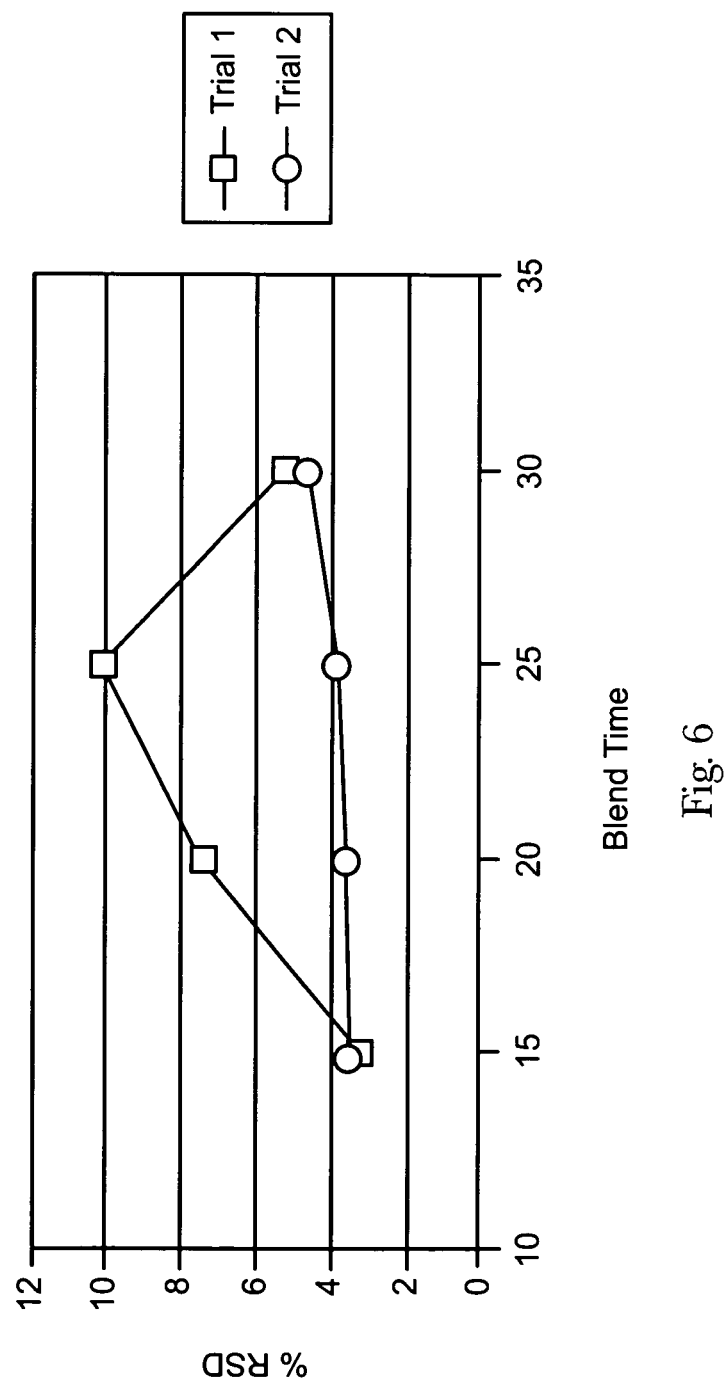
FIG. 6 illustrates content uniformity for the standard and modified processes as a function of blend time.

A similar improvement is observed for content uniformity. FIG. 6 illustrates the improvement in content uniformity obtained with the modified process (trial 2) as a function of blend time for blend times of 15, 20, 25, and 30 minutes as compared with the standard process (trial 1). The corresponding data is given in Table 10 below:

TABLE 9

Content Uniformity of Modified Process (Trial 2).

| Time | Assay | % RSD | L.C. |
|---|---|---|---|
| 15 | 115.4 | 3.34 | 120 |
| 20 | 109.0 | 3.90 | 120 |
| 25 | 114.2 | 3.70 | 120 |
| 30 | 115.1 | 4.64 | 120 |

Figure 7:
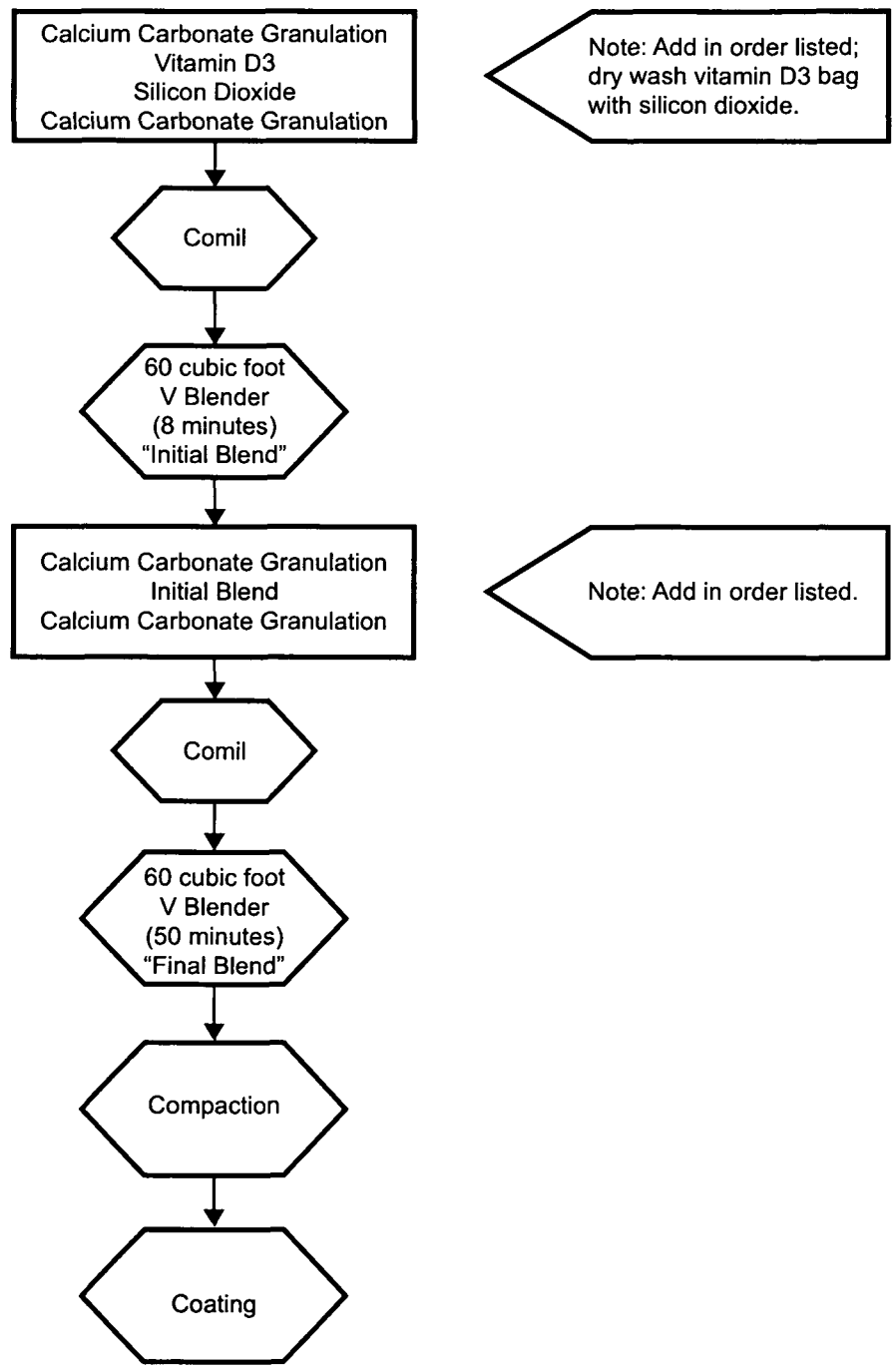
FIG. 7 is the block flow diagram for a large scale process of the modified process.

A large scale method of manufacturing calcium carbonate/vitamin D tablets is developed by forming a premix comprising a layer of calcium carbonate, a layer of vitamin D/silicon dioxide, and another layer of calcium carbonate; sieving and blending the first vitamin D/calcium carbonate granulation mixture in a 60 cubic foot V blender to form a first vitamin D/calcium carbonate granulation mixture; adding calcium carbonate granulation to said premix such that there is a layer of calcium carbonate granulation, a layer of the first vitamin D/calcium carbonate granulation mixture, and another layer of calcium carbonate granulation to form a second vitamin D/calcium carbonate granulation mixture; sieving and blending the second vitamin D/calcium carbonate granulation mixture in a V blender; and, forming tablets from a composition comprising the second vitamin D/calcium carbonate granulation mixture. The first mixture is in a mass ratio of about 1600:20:7 calcium carbonate:vitamin D:silicon dioxide. The step of sieving comprises sieving through a Comil. The step of blending the first mixture in a 60 cubic foot V blender comprises blending for about 8 minutes. The step of adding calcium carbonate granulation to the first mixture may comprise adding two layers of about 500 kg each of calcium carbonate granulation. This process flowchart is given in FIG. 7.

The large scale method further uses the step of milling and sieving the calcium carbonate granulation to produce calcium carbonate and vitamin D granulations having desired particle size characteristics. The milling and sieving of the calcium carbonate leaves a small particle size tail to the distribution. In other words, it generates some fines that spread the distribution towards smaller particle sizes. This is best described in terms of the actual distribution of the particles sizes of the calcium carbonate at the lower end of particle sizes.

The data in Table 10 reports the particle size distribution by segments. The comparative trial example against the four inventive trial examples is highlighted. It can be seen at the lower end (e.g., $D_{16}$ and $D_{20}$) where the grinding lowers the particle size of that segment. So for example, in the comparative trial 20% of the particles have a particle size below 149 microns while for the inventive trials the $D_{20}$ is 92-106 microns. A preferred calcium carbonate granulation is one having a characteristic production of fines, or increase in small particles. Preferably, the calcium carbonate would have a value of $D_{20}$ of below 110 microns and/or a $D_{16}$ value of below 95 microns.

TABLE 10

Particle Size Distribution by Segments.

| | Comparative Example Trial 1 | Inventive Example Trial 2 | Vit D 1 | Vit D 2 | Inventive Example Gran 1 | Inventive Example Gran 2 | Inventive Example Gran 3 |
|---|---|---|---|---|---|---|---|
| D 10 | 134 | n/a | 148 | 139 | n/a | n/a | n/a |
| D 16 | 143 | 90.5 | 158 | 151 | 80.4 | 86 | 77.3 |
| D 20 | 149 | 106 | 164 | 156 | 94.7 | 105 | 92.1 |
| D 30 | 184 | 142 | 179 | 169 | 143 | 170 | 143 |
| D 40 | 228 | 185 | 189 | 182 | 237 | 259 | 208 |
| D 45 | 264 | 216 | 194 | 187 | 290 | 312 | 246 |
| D 50 | 306 | 254 | 199 | 192 | 349 | 376 | 297 |
| D 60 | 412 | 349 | 209 | 204 | 464 | 476 | 362 |
| D 70 | n/a | n/a | 243 | 228 | 565 | 568 | 515 |
| D 80 | n/a | n/a | 294 | 281 | 689 | 679 | 631 |
| D 84 | n/a | n/a | 317 | 306 | 746 | 729 | 685 |
| D 90 | n/a | n/a | 355 | 347 | 840 | 811 | 774 |

The resulting blends are evaluated for content uniformity and the results are given in Table 11.

TABLE 11

Content Uniformity for Large Scale Modified Process.

| Vitamin D Potency | Tablet Label Claim | Vitamin D Overage | Batch Number | % RSD |
|---|---|---|---|---|
| 100,000 IU/g | 400 IU | 10% | 423720 | 5.8 |
| 100,000 IU/g | 400 IU | 10% | 424134 | 5.3 |
| 100,000 IU/g | 400 IU | 10% | 424135 | 5.3 |
| 100,000 IU/g | 400 IU | 10% | 424136 | 7.6 |
| 100,000 IU/g | 400 IU | 20% | 424137 | 5.5 |
| 100,000 IU/g | 400 IU | 20% | 424138 | 3.5 |
| 100,000 IU/g | 400 IU | 20% | 424139 | 5.1 |
| 50,000 IU/g | 400 IU | 0% | 428154 | 3.9 |
| 50,000 IU/g | 400 IU | 0% | 428155 | 1.9 |
| 50,000 IU/g | 400 IU | 0% | 428156 | 3.7 |
| 50,000 IU/g | 400 IU | 10% | 428157 | 2.7 |
| 50,000 IU/g | 400 IU | 10% | 428158 | 4.1 |
| 50,000 IU/g | 400 IU | 10% | 428159 | 3.9 |
| 50,000 IU/g | 800 IU | 0% | 428142 | 2.5 |
| 50,000 IU/g | 800 IU | 0% | 428143 | 2.8 |
| 50,000 IU/g | 800 IU | 0% | 428144 | 4.1 |
| 50,000 IU/g | 800 IU | 10% | 428145 | 2.8 |
| 50,000 IU/g | 800 IU | 10% | 428146 | 3.8 |
| 50,000 IU/g | 800 IU | 10% | 428147 | 3.2 |

It is suspected that the combination of 1) the addition of silicon dioxide in the formulation and 2) the matching of particle size profiles of vitamin D granulation and calcium carbonate granulation results in improved recovery and content uniformity of vitamin D in tablets. This is important from both a quality and regulatory perspective, as nutritional products, such as vitamins, when packaged with pharmaceutical products, must meet all pharmaceutical specifications, including but not limited to those for composite assay and dose uniformity.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of manufacturing calcium carbonate/vitamin D tablets comprising:
    forming a premix comprising a mixture of vitamin D granulation and silicon dioxide;
    adding a calcium carbonate granulation to said premix to form a first vitamin D/calcium carbonate granulation mixture, wherein the calcium carbonate granulation has a median particle size within ±40% of the vitamin D granulation;
    mixing and sieving the first vitamin D/calcium carbonate granulation mixture to form a sieved first vitamin D/calcium carbonate granulation mixture;
    blending the first vitamin D/calcium carbonate granulation mixture in a V blender to form a blended first vitamin D/calcium carbonate granulation mixture;
    dividing the blended first vitamin D/calcium carbonate granulation mixture into four equal portions and adding calcium carbonate to each portion to form a second vitamin D/calcium carbonate granulation mixture;
    blending the second vitamin D/calcium carbonate granulation mixture in a V blender; and,
    forming tablets from a composition comprising the second vitamin D/calcium carbonate granulation mixture.

2. The method of claim 1, wherein said premix of vitamin D and silicon dioxide is in a mass ratio of about 25:9 vitamin D:silicon dioxide.

3. The method of claim 1, wherein said first mixture is in a mass ratio of about 1000:25:9 calcium carbonate:vitamin D:silicon dioxide.

4. The method of claim 1, wherein said step of mixing and sieving comprises sieving through a US 20 Mesh sieve.

5. The method of claim 1, wherein said step of blending the second mixture in a V blender comprises blending for about 2 minutes.

6. The method of claim 1, wherein said step of dividing the first mixture into four equal portions and adding calcium carbonate comprises adding 2.0 kg of calcium carbonate.

7. The method of claim 1, further comprising the step of milling and sieving said calcium carbonate granulation and said vitamin D granulation to produce said calcium carbonate and vitamin D granulations having median particle sizes within ±40% of one another.

8. The method of claim 7, wherein said median particle sizes are within ±25% of one another.

9. The method of claim 7, wherein said median particle sizes are within ±15% of one another.

10. The method of claim 1, further comprising the step of milling and sieving said calcium carbonate granulation to have a $D_{20}$ value of less than 110 microns.

11. The method of claim 1, further comprising the step of milling and sieving said calcium carbonate granulation to have a $D_{16}$ value of less than 95 microns.

12. A method of manufacturing calcium carbonate/vitamin D tablets comprising:
   forming a premix comprising a layer of calcium carbonate, a layer of vitamin D/silicon dioxide and another layer of calcium carbonate, wherein the calcium carbonate has a median particle size within ±40% of the vitamin D;
   sieving and blending the premix to form a first vitamin D/calcium carbonate granulation mixture;
   adding calcium carbonate to said first vitamin D/calcium carbonate granulation mixture such that there is a layer of calcium carbonate granulation, a layer of said first granulation mixture, and another layer of calcium carbonate, to form a second vitamin D/calcium carbonate granulation mixture;
   sieving and blending the second vitamin D/calcium carbonate granulation mixture; and,
   forming tablets from a composition comprising the second vitamin D/calcium carbonate granulation mixture.

13. The method of claim 12, wherein one or both of said steps of sieving and blending the premix and sieving and blending the second vitamin D/calcium carbonate granulation mixture comprises blending with a V blender.

14. The method of claim 13, wherein said step of sieving and blending the premix comprises blending with a V blender comprises blending for about 8 minutes.

15. The method of claim 13, wherein said step of sieving and blending the second vitamin D/calcium carbonate granulation mixture comprises blending with a V blender comprises blending for about 50 minutes.

16. The method of claim 12, wherein said step of forming a premix comprising a layer of calcium carbonate, a layer of vitamin D/silicon dioxide and another layer of calcium carbonate comprises adding two layers of about 500 kg each of calcium carbonate.

17. The method of claim 12, wherein said first mixture is in a mass ratio of about 1600:20:7 calcium carbonate:vitamin D:silicon dioxide.

* * * * *